United States Patent
Raak

(10) Patent No.: US 11,202,456 B1
(45) Date of Patent: Dec. 21, 2021

(54) FOOD ITEM FRESHNESS NOTIFICATION SYSTEM AND RELATED METHODS

(71) Applicant: Inmar Clearing, Inc., Winston-Salem, NC (US)

(72) Inventor: Alise Raak, Winston-Salem, NC (US)

(73) Assignee: INMAR CLEARING, INC., Winston-Salem, NC (US)

( * ) Notice: Subject to any disclaimer, the term of this patent is extended or adjusted under 35 U.S.C. 154(b) by 42 days.

(21) Appl. No.: 16/554,386

(22) Filed: Aug. 28, 2019

(51) Int. Cl.
*A23L 3/3418* (2006.01)
*G01N 33/02* (2006.01)
*A23B 7/152* (2006.01)
*G06Q 10/08* (2012.01)
*G01N 27/12* (2006.01)

(52) U.S. Cl.
CPC ............ *A23L 3/3418* (2013.01); *A23B 7/152* (2013.01); *G01N 27/125* (2013.01); *G01N 33/025* (2013.01); *G06Q 10/087* (2013.01)

(58) Field of Classification Search
CPC ..... A23L 3/3418; A23B 7/152; G01N 27/125; G01N 33/025; G01Q 10/087
See application file for complete search history.

(56) References Cited

U.S. PATENT DOCUMENTS

| | | | |
|---|---|---|---|
| 2004/0213701 A1 | 10/2004 | Hattori et al. | |
| 2016/0162715 A1* | 6/2016 | Luk | F25D 29/005 |
| | | | 235/385 |
| 2018/0279023 A1* | 9/2018 | Taylor | G01N 33/02 |

OTHER PUBLICATIONS

Imspex Diagnostics Limited; "Fruit Rot Detection;" website "www.imspex.com/fruit-rot-detection/"; 2019; pp. 1-2.

* cited by examiner

*Primary Examiner* — Robert J Eom
(74) *Attorney, Agent, or Firm* — Allen, Dyer, Doppelt + Gilchrist, P.A.

(57) ABSTRACT

A food item freshness notification system may include a remote device and a gas sensor configured to sense gas adjacent the food item and generate food item freshness data related thereto. The food item freshness notification system may also include a food item freshness server configured to obtain the food item freshness data from the gas sensor and determine a freshness level for the food item based upon the food item freshness data. The food item freshness server may also be configured to communicate a notification to the remote device based upon the freshness level.

17 Claims, 4 Drawing Sheets

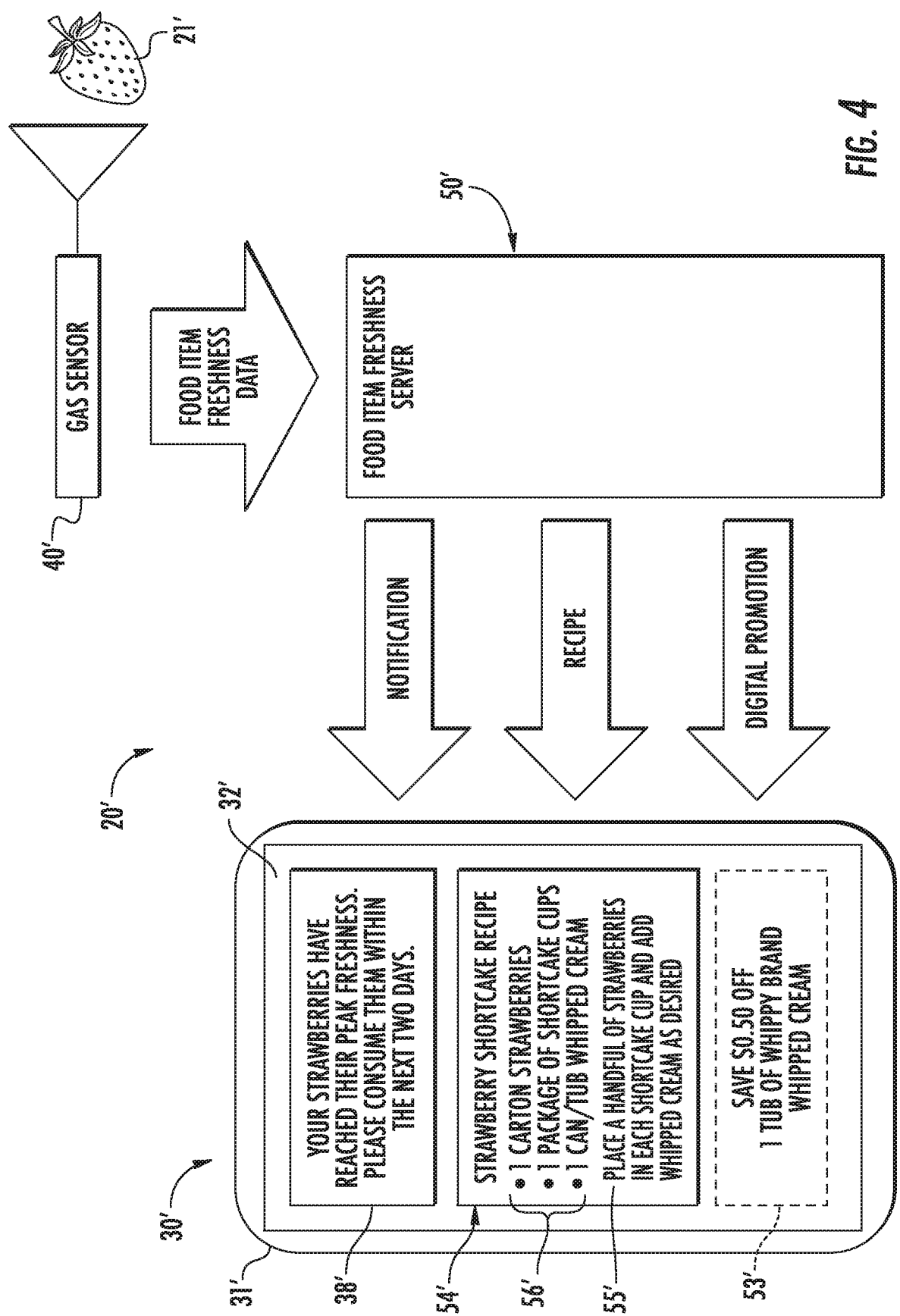

FOOD ITEM FRESHNESS NOTIFICATION SYSTEM AND RELATED METHODS

TECHNICAL FIELD

The present invention relates to the field of food item notifications, and more particularly, to food item freshness based notifications and related methods.

BACKGROUND

Many food items have an associated freshness. For example, many food items sold in a store are stored in a refrigerator after purchase and have a freshness that changes over time. For example, purchased food items in a refrigerator or on a countertop may initially be at or near peak freshness, but as time passes, those same food items become past their peak freshness.

Sales of a particular product or service may be based upon how well that product or service is marketed to a consumer. One form of marketing is a coupon, typically in paper form, for a discount toward the product or service. Some coupons may be retailer specific, for example, only redeemable for the discount at a particular retailer, while other coupons may be product specific from a manufacturer and redeemable at any retailer.

A coupon, while typically in paper form, may be in digital form and may be referred to as a digital promotion. A digital promotion may be selected or "clipped" via a mobile phone and saved to a digital wallet for redemption at a point-of-sale (POS) terminal, for example. A typical coupon is applicable to a given product and has a redeemable value that may vary based upon, for example, the quantity of a given item, brand of item, size of the product in terms of packaging, and/or the price point of the given item. A typical coupon may also be redeemable only at a given retailer and/or within a threshold time period.

U.S. Patent Application Publication No. 2004/0213701 to Hattori et al. is directed to a gas sensor. Further, when using such a semiconductor-type of gas sensor on a refrigerator to sense the freshness or decay of vegetables and fruits, after long-term use of the refrigerator, the gas sensor deteriorates and its output signal is weakened, which sometimes prevents the sensor from sensing the freshness and decay. The weakening (or the deterioration) of the output of the semiconductor type sensor may be attributed to the deterioration with time of its electrodes and catalyst.

SUMMARY

A food item freshness notification system may include a remote device and a gas sensor configured to sense gas adjacent the food item and generate food item freshness data related thereto. The food item freshness notification system may also include a food item freshness server configured to obtain the food item freshness data from the gas sensor and determine a freshness level for the food item based upon the food item freshness data. The food item freshness server may also be configured to communicate a notification to the remote device based upon the freshness level.

The food item freshness server may be configured to generate and communicate a digital promotion for the food item based upon the freshness level. The food item freshness server may be configured to generate the digital promotion to have a value based upon the freshness level, for example.

The notification may include a recipe that includes instructions and a plurality of food ingredients, and the food item may be one of the plurality of food ingredients. The food item freshness server may be configured to generate and communicate a digital promotion for one of the plurality of food ingredients other than the food item, for example.

The food item freshness server may be configured to determine a peak-freshness level, and generate and communicate the notification within a threshold time from the peak-freshness level. The food item freshness server may be configured to cooperate with the remote device to prompt for purchase of the food item, for example. The remote device may include a mobile wireless communications device, for example.

A method aspect is directed to a method of notifying a freshness level of a food item. The method may include using a food item freshness server to obtain food item freshness data related to the food item from a gas sensor configured to sense gas adjacent the food item and determine the freshness level for the food item based upon the food item freshness data. The method may also include using the food item freshness server to communicate a notification to a remote device based upon the freshness level.

A computer readable medium aspect is directed to a non-transitory computer readable medium for notifying a freshness level of a food item. The non-transitory computer readable medium includes computer executable instructions that when executed by a processor cause the processor to perform operations. The operations may include obtaining food item freshness data related to the food item from a gas sensor configured to sense gas adjacent the food item and determining the freshness level for the food item based upon the food item freshness data. The operations may also include communicating a notification to a remote device based upon the freshness level.

BRIEF DESCRIPTION OF THE DRAWINGS

FIG. 4 is a schematic diagram of a food item freshness notification system in accordance with another embodiment.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
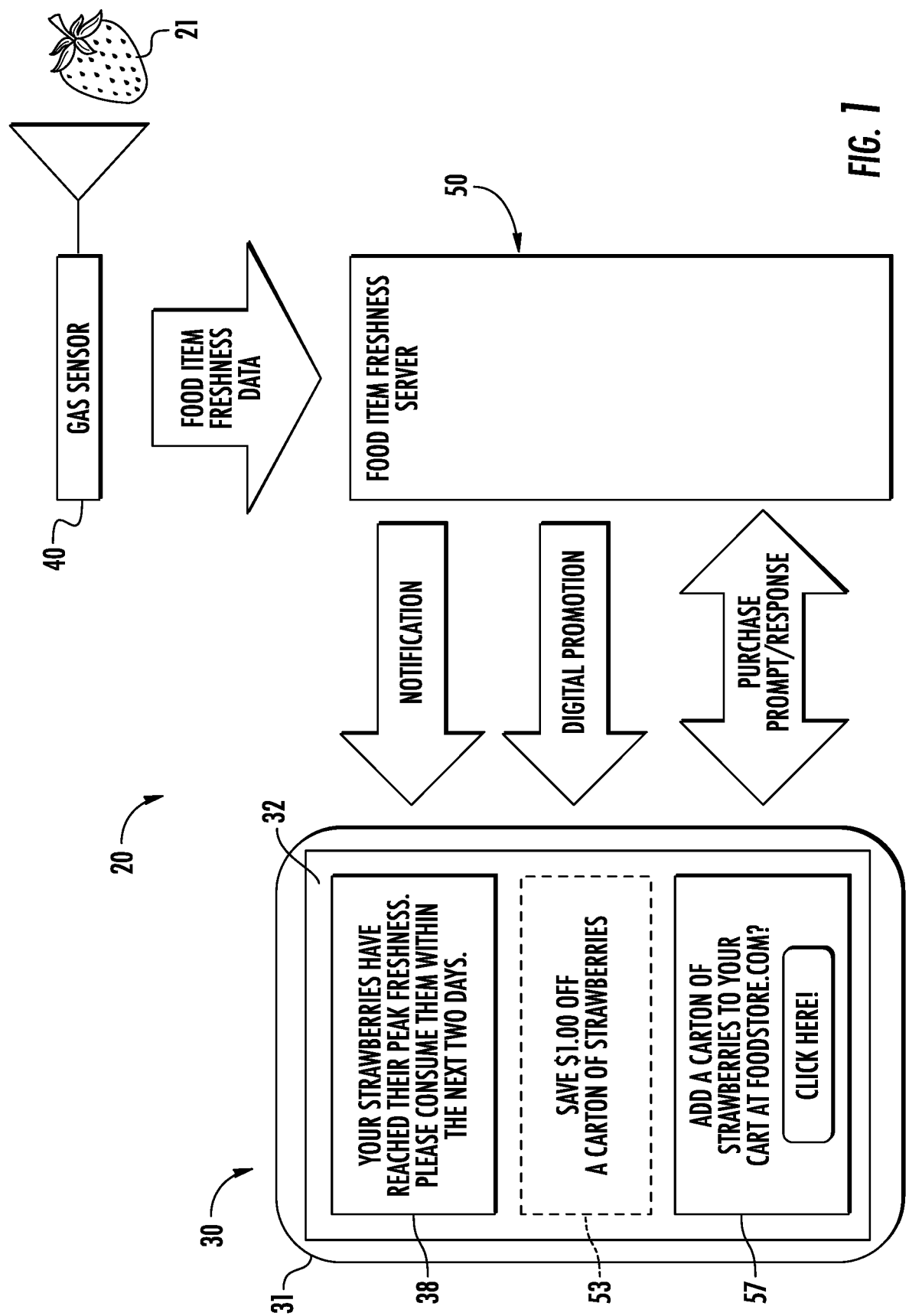
FIG. 1 is a schematic diagram of a food item freshness notification system in accordance with an embodiment.
Figure 2:
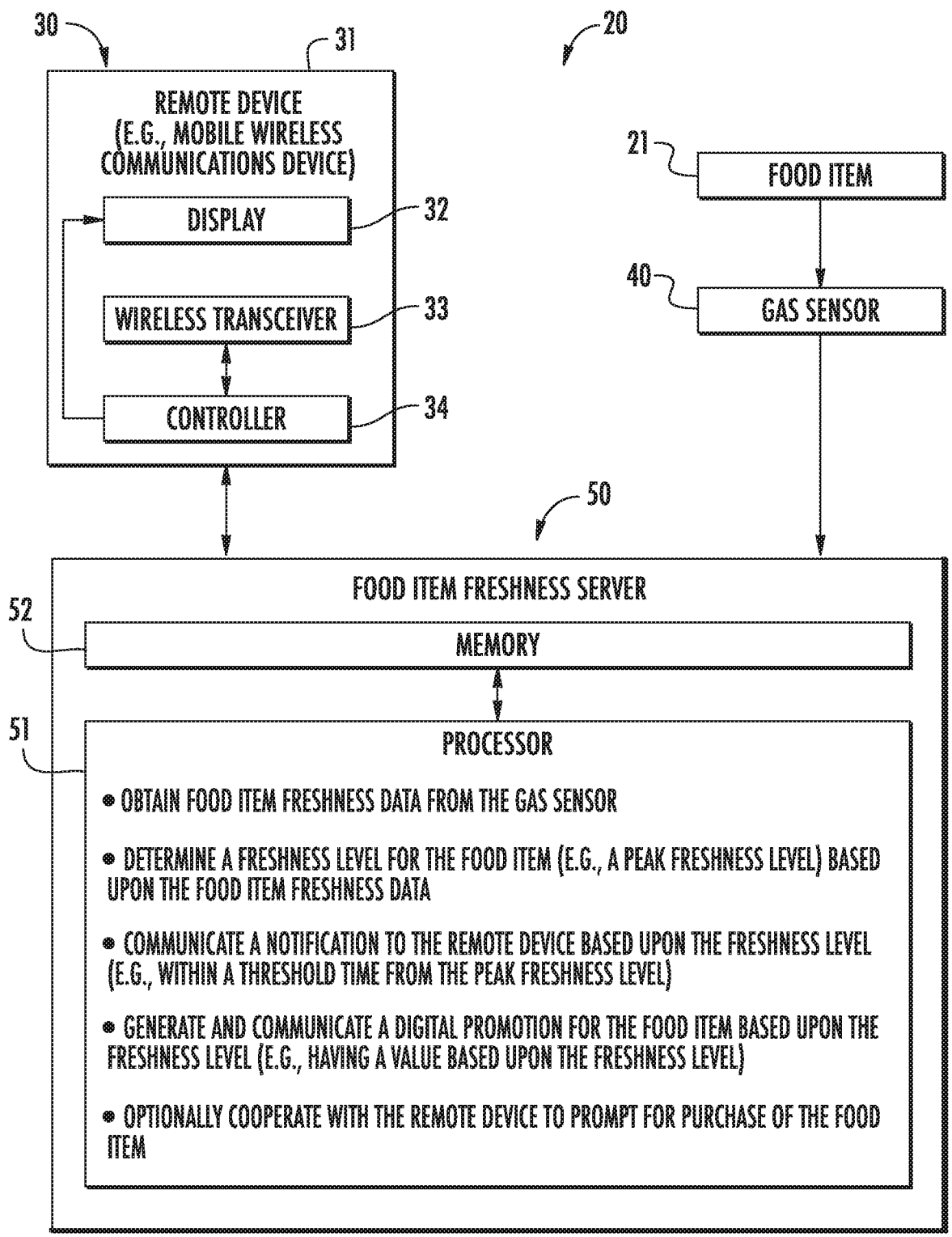
FIG. 2 is a schematic block diagram of the food item freshness notification system of FIG. 1.

Referring initially to FIGS. 1 and 2, a food item freshness notification system 20 includes a remote device 30. The remote device 30 is illustratively in the form of a mobile wireless communications device that includes a housing 31, a display 32 carried by the housing, a wireless transceiver 33 carried by the housing, and a remote device controller 34 coupled to the display and the wireless transceiver. The remote device 30 may be in the form of another type of device, for example, a personal computer, a tablet computer, a laptop computer, or a wearable device.

The food item freshness notification system 20 also includes a gas sensor 40. The gas sensor 40 senses gas adjacent the food item 21 and generates food item freshness data related to the food item. The gas sensor 40 may sense gas and/or generate the food item freshness data continuously or at predetermined intervals, for example, hourly, daily, etc.

Those skilled in the art will appreciate that the gas sensor 40 may include a gas chromatograph. An exemplary gas sensor 40 may be the GC-IMS™ system available from IMSPEX Diagnostic Limited of Santa Clara, Calif. The gas sensor 40 may include gas transport tubes and/or other gas transport elements so that the gas sensor may be remote from or at a distance from the food item 21. The food item freshness data may include raw data from the gas sensor 40. The food item freshness data may include other and/or additional data indicative of freshness, for example, relative freshness.

The food item freshness notification system 20 also includes a food item freshness server 50. The food item freshness server 50 includes a processor 51 and a memory 52 cooperating therewith. While operations of the food item freshness server 50 are described herein, those skilled in the art will appreciate that the processor 51 and the memory 52 cooperate to perform the operations.

Figure 3:
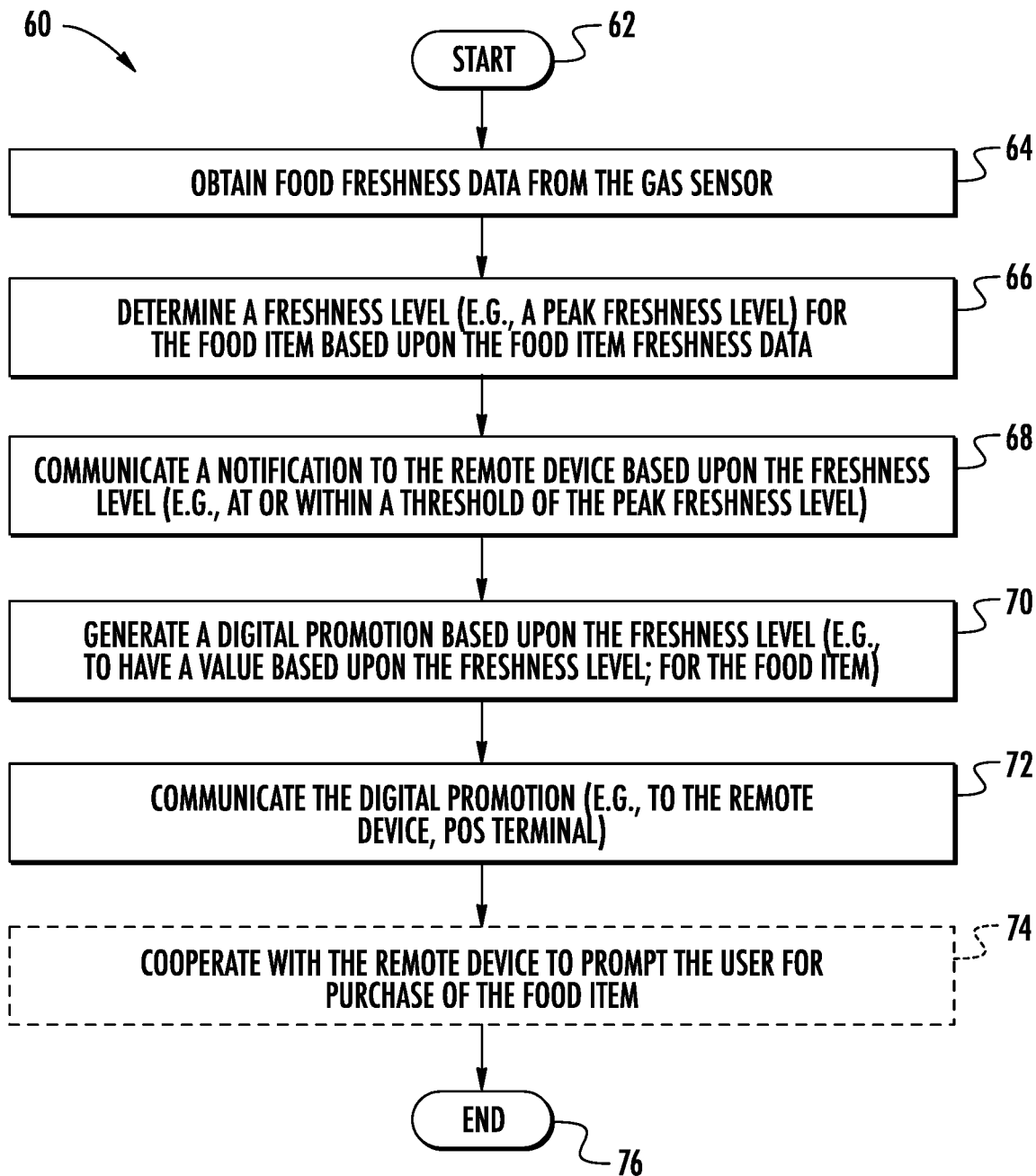
FIG. 3 is a flow diagram illustrating operation of the food item freshness server of FIG. 2.

Referring now additionally to the flowchart 60 in FIG. 3, beginning at Block 62, operations of the food item freshness server 50 will now be described. At Block 64, the food item freshness server 50 obtains the food item freshness data from the gas sensor 40.

The food item freshness server 50 determines a freshness level for the food item 21 based upon the food item freshness data (Block 66). The freshness level may be based upon current freshness data relative to reference or baseline freshness data when the food item 21 is freshest. The freshness level may also be based upon the type of food item, which may be sensed by the gas sensor 40 and/or may be identified by the user, for example, by way of the remote device 30. The food item freshness server 50 may thus determine, based upon the food item freshness data, when the food item 21 is at a peak-freshness level. In some embodiments, the food item freshness server 50 may determine when a threshold amount of freshness of the food item 21 remains (e.g., remaining shelf life).

At Block 68, the food item freshness server 50 communicates a notification 38 to the remote device 30 based upon the freshness level. For example, the notification 38 may be a textual notification (FIG. 1). The notification 38 may be in the form of a color-coded indicator or icon on the display 32 of the remote device 30 that corresponds to the freshness of the food item 21 (e.g., red=not fresh, green=fresh, yellow=moderately fresh). In some embodiments, where the food item freshness server 50 determines the peak-freshness, the food item freshness server may generate the notification 38 based upon the peak-freshness. In other words, the food item freshness server 50 may communicate the notification 38 at or within a threshold time period of the peak-freshness.

At Block 70, the food item freshness server 50 generates a digital promotion 53 based upon the freshness level. The food item freshness server 50 may generate the digital promotion 53 based upon a decreasing freshness level (e.g., anytime beyond peak freshness). The digital promotion 53 may be for the food item 21, for example, for an amount off the purchase of the food item (FIG. 1).

At Block 72, the food item freshness server 50 communicates the digital promotion 53, for example, to the remote device 30 for display thereon. The digital promotion 53 may be presented for redemption during checkout at a point-of-sale (POS) terminal or within an electronic commerce (e-commerce) platform. The digital promotion 53 may be saved, for example, in a digital wallet, for future redemption. In some embodiments, the food item freshness server 50 may generate the digital promotion 53 to have a value that is based upon the freshness level. More particularly, for example, where the food item freshness server 50 communicates the notification 38 upon a threshold freshness, the digital promotion 53 may have a value that is larger when the food item 21 is less fresh (i.e., the notification is communicated later with respect to freshness relative to a peak freshness, for example). In some embodiments, the food item freshness server 50 may generate and communicate a digital promotion 53.

At Block 74, the food item freshness server 50 optionally cooperates with the remote device 30 to prompt the user for purchase of the food item 21. More particularly, the food item freshness server 50 may cooperate with the remote device 30 so that a prompt 57 is displayed on the display 32 of the remote device asking whether the user wishes to purchase the food item 21. If the user or shopper is desirous of purchasing the food item 21, the user may provide input via the remote device 30 indicative of such (e.g., via the touch display 32), and the food item may be added to a virtual shopping cart on an e-commerce platform, for example, which may or may not be part of the food item freshness server 50. Operations end at Block 76.

Referring now to FIG. 4, in another embodiment, the notification 38' may include a recipe 54' that includes instructions 55' and food ingredients 56'. The food item 21' is one of the food ingredients 56'. The food item freshness server 50' may communicate the notification 38' or recipe 54' at or within a desired freshness level. For example, if a shopper's bananas are determined to be past peak freshness, the food item freshness server 50' may communicate a recipe 54' for banana bread, or if a shopper's strawberries are determined to be past peak freshness, the food item freshness server may communicate a recipe for strawberry shortcake. The food item freshness server 50' may communicate a digital promotion 53' to the remote device 30' for another item other than the food item 21' determined to be past peak-freshness (e.g., for another food item other than bananas in the banana bread recipe or strawberries in the strawberry shortcake examples above). Of course, the digital promotion 53' may be for the food item 21' (i.e., the bananas or strawberries in the above example).

A method aspect is directed to a method of notifying a freshness level of a food item 21. The method may include using a food item freshness server 50 to obtain food item freshness data related to the food item 21 from a gas sensor 40 configured to sense gas adjacent the food item and determine the freshness level for the food item based upon the food item freshness data. The method may also include using the food item freshness server 50 to communicate a notification 38 to a remote device 30 based upon the freshness level.

A computer readable medium aspect is directed to a non-transitory computer readable medium for notifying a freshness level of a food item 21. The non-transitory computer readable medium includes computer executable instructions that when executed by a processor 51 cause the processor to perform operations. The operations may include obtaining food item freshness data related to the food item 21 from a gas sensor 40 configured to sense gas adjacent the food item and determining the freshness level for the food item based upon the food item freshness data. The operations may also include communicating a notification 38 to a remote device 30 based upon the freshness level.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A food item freshness notification system comprising:
   a mobile wireless communications device comprising one of a smartphone, tablet computer, and a wearable device;
   a gas sensor configured to sense gas adjacent a food item and generate current food item freshness data related thereto; and
   a food item freshness server configured to
      obtain the current food item freshness data from the gas sensor,
      determine a freshness level for the food item based upon the current food item freshness data relative to a baseline freshness data when the food item is freshest,
      generate a digital coupon for the food item based upon the freshness level, the digital coupon having a redeemable value associated therewith redeemable toward purchase of the food item at a point-of-sale (POS) terminal, the redeemable value being determined based upon the freshness level so that the redeemable value is larger when the food item is less fresh,
      communicate the digital coupon to the mobile wireless communications device, and
      communicate a notification to the mobile wireless communications device based upon the freshness level.

2. The system of claim 1 wherein the food item freshness server is configured to generate the digital coupon to have the redeemable value based upon the freshness level.

3. The system of claim 1 wherein the notification comprises a recipe comprising instructions and a plurality of food ingredients; and wherein the food item is one of the plurality of food ingredients.

4. The system of claim 1 wherein the food item freshness server is configured to determine a peak-freshness level, and generate and communicate the notification within a threshold time from the peak-freshness level.

5. The system of claim 1 wherein the food item freshness server is configured to cooperate with the mobile wireless communications device to prompt for purchase of the food item.

6. A food item freshness server comprising:
   a processor and an associated memory configured to
      obtain current food item freshness data related to a food item from a gas sensor configured to sense gas adjacent the food item,
      determine a freshness level for the food item based upon the current food item freshness data relative to a baseline freshness data when the food item is freshest,
      generate a digital coupon for the food item based upon the freshness level, the digital coupon having a redeemable value associated therewith redeemable toward purchase of the food item at a point-of-sale (POS) terminal, the redeemable value being determined based upon the freshness level so that the redeemable value is larger when the food item is less fresh,
      communicate the digital coupon to a mobile wireless communications device comprising one of a smartphone, tablet computer, and a wearable device, and
      communicate a notification to the mobile wireless communications device based upon the freshness level.

7. The server of claim 6 wherein the processor is configured to generate the digital coupon to have the redeemable value based upon the freshness level.

8. The server of claim 6 wherein the notification comprises a recipe comprising instructions and a plurality of food ingredients; and wherein the food item is one of the plurality of food ingredients.

9. The server of claim 6 wherein the processor is configured to determine a peak-freshness level, and generate and communicate the notification within a threshold time from the peak-freshness level.

10. The server of claim 6 wherein the processor is configured to cooperate with the mobile wireless communications device to prompt for purchase of the food item.

11. A method of notifying a freshness level of a food item comprising:
    using a food item freshness server to
       obtain current food item freshness data related to the food item from a gas sensor configured to sense gas adjacent the food item,
       determine the freshness level for the food item based upon the current food item freshness data relative to a baseline freshness data when the food item is freshest,
       generate a digital coupon for the food item based upon the freshness level, the digital coupon having a redeemable value associated therewith redeemable toward purchase of the food item at a point-of-sale (POS) terminal, the redeemable value being determined based upon the freshness level so that the redeemable value is larger when the food item is less fresh,
       communicate the digital coupon to a mobile wireless communications device comprising one of a smartphone, tablet computer, and a wearable device, and
       communicate a notification to the mobile wireless communications device based upon the freshness level.

12. The method of claim 11 wherein the notification comprises a recipe comprising instructions and a plurality of food ingredients; and wherein the food item is one of the plurality of food ingredients.

13. The method of claim 12 wherein using the food item freshness server comprises using the food item freshness server to generate and communicate the digital coupon for one of the plurality of food ingredients other than the food item.

14. A non-transitory computer readable medium for notifying a freshness level of a food item, the non-transitory computer readable medium comprising computer executable instructions that when executed by a processor cause the processor to perform operations comprising:

obtaining current food item freshness data related to the food item from a gas sensor configured to sense gas adjacent the food item;

determining the freshness level for the food item based upon the current food item freshness data relative to a baseline freshness data when the food item is freshest;

generating a digital coupon for the food item based upon the freshness level, the digital coupon having a redeemable value associated therewith redeemable toward purchase of the food item at a point-of-sale (POS) terminal, the redeemable value being determined based upon the freshness level so that the redeemable value is larger when the food item is less fresh;

communicating the digital coupon to a mobile wireless communications device comprising one of a smartphone, tablet computer, and a wearable device; and communicating a notification to the mobile wireless communications device based upon the freshness level.

15. The non-transitory computer readable medium of claim 14 wherein the operations comprise generating the digital coupon to have the redeemable value based upon the freshness level.

16. The non-transitory computer readable medium of claim 14 wherein the notification comprises a recipe comprising instructions and a plurality of food ingredients; and wherein the food item is one of the plurality of food ingredients.

17. The non-transitory computer readable medium of claim 16 wherein the operations comprise generating and communicating the digital coupon for one of the plurality of food ingredients other than the food item.

* * * * *